United States Patent [19]

Kraus et al.

[11] Patent Number: 5,446,192
[45] Date of Patent: Aug. 29, 1995

[54] PROCESS FOR THE PREPARATION OF β-AMINOACRYLIC ACID ESTERS

[75] Inventors: Helmut Kraus, Köln; Heinz-Ulrich Blank, Odenthal; Gerhard Marzolph, Köln, Germany

[73] Assignee: Bayer Aktiengesellschaft, Leverkusen, Germany

[21] Appl. No.: 25,489

[22] Filed: Mar. 3, 1993

[30] Foreign Application Priority Data

Mar. 12, 1992 [DE] Germany ............. 42 07 852.0

[51] Int. Cl.$^6$ .......................... C07C 229/00
[52] U.S. Cl. ...................... 560/172; 544/171; 546/341; 548/573; 560/38; 560/43; 560/125
[58] Field of Search ............ 560/172, 38, 43, 125; 544/171; 546/341; 548/573

[56] References Cited

U.S. PATENT DOCUMENTS

| | | | |
|---|---|---|---|
| 2,578,788 | 12/1951 | Benneville | 560/172 |
| 2,987,491 | 6/1961 | Bader | 560/172 |
| 3,420,827 | 1/1969 | Leffingwell | 560/172 |
| 4,027,037 | 5/1977 | Siegle | 560/172 |
| 4,772,711 | 9/1988 | Englaender et al. | |
| 5,030,747 | 7/1991 | Blank et al. | |
| 5,196,541 | 3/1993 | Gayer et al. | |

FOREIGN PATENT DOCUMENTS 0217018 4/1987 European Pat. Off. .
0388744 9/1990 European Pat. Off. .

OTHER PUBLICATIONS

Tetrahedron Letters, vol. 27, No. 23, pp. 2567–2570, 1986; "The Synthesis of Mannich Bases from Ketones and Esters Via Enaminones", Paul Francis Schuda et al. Tetrahedron Letters No. 45, pp. 4061–4064, 1976.
Liebigs Annalen Der Chemie, vol. 1980, No. 7 pp. 997–1180.
Chem. ber. 104, pp. 2709–2726, 1971.
H. Saur, Thesis, Univ. Stuttgart 1971, p. 41.
Org. Prep. Proced. Int. 10, (1978), pp. 67–72.

*Primary Examiner*—Michael L. Shippen
*Attorney, Agent, or Firm*—William C. Gerstenzang; Sprung Horn Kramer & Woods

[57] ABSTRACT

β-Aminoacrylic acid esters can be prepared by reacting acetic acid esters of the formula $$H_2CR_1\text{—}COOR^2 \quad (II)$$

with aminal esters of the formula

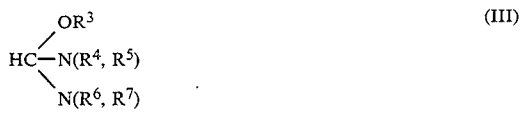

at 0.5–10 bar and 50°–170° C. in an aprotic polar solvent.

The radicals $R^1$ to $R^7$ are as defined in the description.

18 Claims, No Drawings

PROCESS FOR THE PREPARATION OF β-AMINOACRYLIC ACID ESTERS

BACKGROUND OF THE INVENTION

The present invention relates to a process for the preparation of β-aminoacrylic acid esters from acetic acid esters and aminal esters (alkoxybis-(dialkylamino)methanes).

A number of possible ways of preparing β-aminoacrylic acid esters are known. An interesting industrial route is the reaction of amines with alkali metal salts of β-hydroxy-acrylic acid esters, which are obtainable from CO, alcoholate and acetic acid esters in a pressure reaction requiring 20 to 50 bar. This route, known in principle from Annales de Chimie 18 (1932), 108, was improved to a total yield of about 70% in European Patent Specification 217 018. European Patent Specification 388 744 describes another variant with yields of 85 to 95% of the theoretical yield. In each of these cases, the reaction has to be carried out in high-pressure apparatuses; the high toxicity and the flammability of the CO requires special safety devices.

Highly toxic iron pentacarbonyl is used in the reaction of methyl acrylates with t-butoxy-bis-(dimethylamino)-methane (Tetrahedron Lett. 1976, 4061; An. Chem. 1980, 991). In addition, the polymerisation of the acrylic acid ester, which makes the reaction product more difficult to isolate, must be taken into account in this process.

The reaction of t-butoxy-bis-(dimethylamino)-methane with ethyl acetate (Chem. Ber. 104, 1971, 2709) gives 88% of β-dimethylaminoacrylic acid ester after 20 hours at 170° C. To achieve this, however, the process has to be carried out in a sealed tube and high pressures are attained at the end of the reaction due to the alcohol and dimethylamine produced. On further investigation of this reaction, it was found that when it is carried out in a 250 ml or 500 ml autoclave, only 60% of the theoretical yield is obtained (H. Saur, Thesis, Univ. Stuttgart 1971, p. 41). When a 50% excess of ethyl acetate is , used, β-dimethylaminoacrylic acid ester is no longer formed, a higher-boiling substance being obtained instead. When methoxy-bis-(dimethylamino)-methane is reacted with ethyl butyrate, no reaction product is obtained at all (Org. Prep. Proceed. Int. 10, (1978), 67).

SUMMARY OF THE INVENTION

With the knowledge contained in the literature on the reactivity of ortho-amides with carboxylic acid esters, it was therefore surprising that the reaction to give the aminomethyleneated derivatives can be carried out in a pressure range from subatmospheric pressure to only a moderately increased pressure and without the use of pressure vessels.

A process for the preparation of β-aminoacrylic acid esters of the formula $$(R^4,R^5)N-CH=CR^1-COOR^2 \quad (I)$$

by reacting acetic acid esters of the formula $$H_2CR_1-COOR^2 \quad (II)$$

with aminal esters of the formula

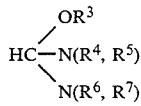

in which formulae $R^1$ is hydrogen, linear or branched $C_1-C_8$-alkyl, linear or branched $C_2-C_8$-alkenyl, $C_3-C_8$-cycloalkyl, $C_6-C_{12}$-aryl, $C_7-C_{10}$-aralkyl or a 5–8-membered aromatic or non-aromatic heterocyclic ring in which the heteroatoms are 1 or 2 from the group consisting of N, O or S, $R^2$ and $R^3$ independently of one another are linear or branched $C_1-C_8$-alkyl and $R^4$, $R^5$, $R^6$ and $R^7$ independently of one another are linear or branched $C_1-C_8$-alkyl, linear or branched $C_2-C_8$-alkenyl, $C_2-C_8$-alkoxyalkyl, $C_3-C_8$-alkoxyalkenyl, $C_3-C_8$-cycloalkyl, $C_6-C_{12}$-aryl, $C_7-C_{10}$-aralkyl or a 5–8membered aromatic or non-aromatic heterocyclic ring in which the heteroatoms are 1 or 2 from the group consisting of N, O or S, it further being possible for $R^4$ and $R^5$ or $R^6$ and $R^7$, together with the N atom which they substitute, to form a 5–8 -membered aromatic or non-aromatic N-heterocyclic ring which can contain another heteroatom from the group consisting of N, O and S, has been found which is characterised in that the reaction is carried out at 0.5 to 10 bar, preferably 1 to 5 bar, and at 50°–170° C., preferably at 80°–150° C. in an aprotic polar solvent preferably determined from the group N-persubstituted acid amides, sulpholanes, sulphoxides and sulphones.

DETAILED DESCRIPTION OF THE INVENTION

The reaction of the process according to the invention can be represented in the general form as follows:

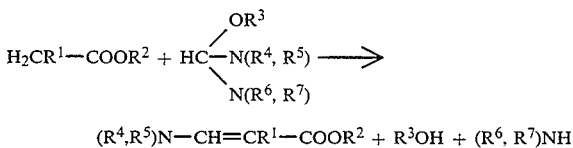

$$(R^4,R^5)N-CH=CR^1-COOR^2 + R^3OH + (R^6, R^7)NH$$

Linear or branched $C_1-C_8$-alkyl is for example methyl, ethyl, propyl, isopropyl, butyl, isobutyl, tert-butyl, the isomeric amyls, hexyls or octyls, preferably said $C_1-C_4$-alkyl radicals, particularly preferably methyl or ethyl and very particularly preferably methyl.

$C_2-C_8$-Alkenyl is vinyl, propenyl, allyl, the isomeric butenyls, amylenyls, hexenyls or octenyls, preferably said $C_3-C_4$-alkenyl radicals.

$C_2-C_8$-Alkoxyalkyl is for example methoxymethyl, ethoxy-methyl, methoxyethyl and other radicals from the group consisting of $C_3-C_9$-alkyl in which a $CH_2$ group is replaced with an O atom.

$C_3-C_8$-Alkoxyalkenyl is for example methoxyvinyl, ethoxyvinyl, methoxyallyl, 2-methoxy-propenyl and other radicals from the group consisting of $C_4-C_9$-alkenyl in which a $CH_2$ group is replaced with an O atom.

$C_3-C_8$Cycloalkyl is for example cyclopropyl, methylcyclopropyl, dimethyl-cyclopropyl, cyclobutyl, methylcyclobutyl, cyclopentyl, methyl-cyclopentyl, cyclohexyl, methyl-cyclohexyl, dimethyl-cyclohexyl, cycloheptyl or cyclooctyl, preferably cyclopropyl, cyclopentyl and cyclohexyl, as well as their methyl or dimethyl derivatives.

$C_6$—$C_{12}$-Aryl is for example phenyl, naphthyl or biphenylyl, preferably phenyl.

$C_7$—$C_{10}$-Aralkyl is for example benzyl, 1-phenylethyl, 2-phenylethyl and other radicals of this type known to those skilled in the art, preferably benzyl.

The following may be mentioned as 5- to 8-membered aromatic or non-aromatic heterocyclic rings in which the heteroatoms are 1 or 2 from the group consisting of N, O and S: pyrrole, furan, thiophene, pyrrolidine, pyrazole, imidazole, thiazole, oxazole, pyridine, pyrimidine, piperazine, morpholine, pyran, azepine, azocine, isoxazole, isothiazole, pyridazine and pyrazine.

Furthermore, $R^4$ and $R^5$ $R^6$ $R^7$, together with the N atom which they substitute, can form a 5- to 8-membered aromatic or non-aromatic ring which can contain another heteroatom from the group consisting of N, O and S. Examples of such systems are pyrrole, pyrrolidine, pyrroline, pyrazole, pyrazolidine, imidazole, imidazolidine, thiazole, thiazolidine, piperazine, piperidine, morpholine, azepine and dihydroazocine.

Said radicals can in turn be substituted by $C_1$—$C_4$-alkyl, preferably methyl, by $C_1$—$C_4$-alkoxy, preferably methoxy, by halogen such as chlorine, fluorine or bromine, or by phenyl or hydroxyl. Other substituents, especially for the aromatic moieties of said radicals and substituents, are typically aromatic substituents such as nitro or cyano. The heterocyclic radicals can be fused with a benzene ring.

Radicals which may be mentioned for $R^1$ are preferably hydrogen or linear or branched $C_1$—$C_4$-alkyl, particularly preferably hydrogen and methyl. Radicals which may be mentioned for $R^2$ are preferably linear or branched $C_1$—$C_4$-alkyl, particularly preferably methyl or ethyl. Radicals which may be mentioned for $R^3$ are preferably linear or branched $C_1$—$C_5$-alkyl.

In another preferred embodiment, $R^4$, $R^5$, $R^6$ and $R^7$ independently of one another are linear or branched $C_1$—$C_4$-alkyl, cyclopropyl, cyclopentyl, cyclohexyl, phenyl or benzyl, it further being possible for $R^4$ and $R^5$ or $R^6$ and $R^7$, together with the N atom which they substitute, to form a 5- to 8-membered aromatic or non-aromatic N-heterocyclic ring which can contain another heteroatom from the group consisting of N, O and S. Particularly preferably, $R^4$ to $R^7$ independently of one another are linear or branched $C_1$—$C_4$-alkyl or $R^4$ and $R^5$ or $R^6$ and $R^7$, together with the N atom which they substitute, are morpholino, pyrrolidino or piperidino.

By virtue of the low pressure requirement of the process according to the invention, it is possible for the first time to carry out this interesting reaction under favourable industrial conditions.

Solvents for the process according to the invention are aprotic and polar substances. Such substances are taken for example from the group consisting of N-persubstituted acid amides such as dimethylformamide (DMF), dimethyl-acetamide (DMAC), diethylacetamide and homologues thereof, N-methyl-pyrrolidone (NMP), N-methyl-caprolactam (NMC), hexamethylphosphoramide, tetramethylurea and the like; the group consisting of sulpholane and its derivatives substituted by methyl, ethyl and other inert substituents; the group consisting of sulphoxides such as dimethyl sulphoxide, diethyl sulphoxide and the like; and the group consisting of sulphones such as diethyl sulphone, dimethyl sulphone and the like. As the starting materials and the reaction products of the process according to the invention are also of a polar and aprotic nature, it is possible to use an excess of these as solvents and diluents inherent in the system. It is even possible to fully dispense with aprotic polar solvents foreign to the system. In the case where a foreign solvent is used, those which may be mentioned are preferably an N-persubstituted acid amide, particularly preferably NMP, NMC, DMAC, DMF or tetramethyl-urea, and very particularly preferably DMF.

The temperature range for the process according to the invention is from 50° to 170° C. preferably from 80° to 150° C.

The aminal ester and the acetic acid ester are reacted in a molar ratio of 3:1 to 1:10, preferably 2:1 to 1:5 and particularly preferably 1:1 to 1:4.

As well as the pure compound, the aminal ester used can also be the dismutation mixture of amide acetal, aminal ester and tris-(dialkylamino)-methane, which can be present in a ratio of 0:1:0 to 0.33:0.33:0.33. Depending on the preparation, a higher proportion of amide acetal is also possible and permissible; it varies in the range from 0 to 20% by weight of the total amount by weight of the aminal ester or of the pure dismutation mixture. These interrelationships are known to those skilled in the art.

The reaction conditions of the aminomethyleneation of substituted acetic acid esters within the framework of the process according to the invention can easily be adapted to the reactivity of the reactants different substituents. Thus the reactivity of the aminal esters increases if the alkoxy radical $R^3$ changes from a primary through a secondary to a tertiary radical. For tertiary aminal esters, normal pressure is sufficient if the reaction is carried out in a polar aprotic solvent, preferably in DMF. No additional solvent is necessary in the case of aryl-substituted acetic acid esters; it is sufficient to use an excess of the ester in question. When using primary aminal esters, whose manufacturing costs are more favourable, the reaction will be carried out in the upper part of said temperature range; even here, however, it is not necessary to raise the pressure to more than 10 bar, preferably to more than 5 bar. The alkoxy group of the aminal ester should correspond to that of the acetic acid ester; otherwise a very slight transesterification can take place.

It has furthermore been found—and this constitutes an advantageous embodiment of the process according to the invention—that the described reaction of acetic acid esters with aminal esters can be catalysed by one or more compounds from the groups consisting of tertiary aromatic amines and tertiary aromatic carbinols of the formulae

$$Ar^1\text{—}N(R^8,R^9) \quad \text{(IV)}$$

and

$$Ar^2\text{—}\underset{R^{11}}{\overset{R^{10}}{C}}\text{—OH,} \quad \text{(V)}$$

in which formulae

R[8] and R[9] independently of one another have the abovementioned range of meanings of $R^4$ and $R^5$, $Ar^1$ and $Ar^2$ independently of one another are 5- to 7-membered carbocyclic or heterocyclic aromatic radicals which can also be substituted in the abovementioned manner, $R^{10}$ has the range of meanings of $R^4$ and $R^{11}$ has the range of meanings of $R^4$ or $Ar^2$ but is independent of $R^4$ and $Ar^2$.

Examples of suitable radicals $Ar^1$ and $Ar^2$ are phenyl, biphenyl, nitrophenyl, chlorophenyl, tolyl, xylyl, pyridyl, picolyl, chloropyridyl, thiophenyl and pyrryl.

The catalyst or a mixture of several catalysts is used in an amount of 0.1 to 10 mol %, preferably 0.5 to 5 mol %, based on the aminal ester. Here the aminal ester and acetic acid ester are generally introduced first and the catalyst added afterwards.

The successful use of said catalysts is surprising since it is known that although cyclic secondary amines increase the reactivity of DMF dimethyl acetal, they give a mixture of dialkylamino and cyclic aminomethylene compounds. This accelerating effect of cyclic secondary amines on the reaction has also been confirmed in the case of condensation reactions with aminal esters, but again a mixture of the aminoacrylic acid esters is obtained. Aliphatic tertiary amines, such as triethylamines, which are supposed to catalyse reactions with the DMF acetal, have proved ineffective with the aminal ester.

When the reaction mixture is worked up, catalysts are obtained in the bottom of the distillation column. The catalysts remaining in the bottom of the distillation column are reusable.

EXAMPLE 1

150 ml of DMF and 120 ml of ethyl acetate were added to 123 g of t-butylaminal ester (0.1:0.8:0.1 dismutation mixture) and the mixture was refluxed for 4 h. After distillation of the volatile constituents, firstly DMF and then ethyl β-dimethylaminoacrylate were distilled over under vacuum to give 100.7 g of 99.2% pure product, corresponding to 98.8% of the theoretical yield.

EXAMPLE 2

In a distillation apparatus, 86 g of t-butylaminal ester and 87 g of ethyl butyrate in 100 ml of DMF were heated so that the alcohol distilled off slowly. Distillation of the product gave 73.8 g of ethyl β-dimethylamino-2ethylacrylate, corresponding to 87.3% of the theoretical yield.

EXAMPLE 3

In a 300 ml V₄A autoclave, 34.6 g of 96% methylaminal ester, 28 g of methyl acetate and 1.5 g of 4-dimethylamino-pyridine in 80 ml of DMF were heated at 130° C. for 8 h. The maximum pressure was 5 bar and the yield was 89.7% of the theoretical yield.

EXAMPLE 4

The experiment of Example 3 was carried out with ethyl acetate to give 74.5% of ethyl β-dimethylaminoacrylate and 17.6% of the corresponding methyl ester.

EXAMPLE 5

In the experiment of Example 3, 2.5 g of 1,1-diphenylmethanol were added instead of 4-dimethylamino-pyridine to give 88.2% of the theoretical yield of methyl β-dimethylamino-acrylate.

EXAMPLE 6

The experiment of Example 3 was carried out without a catalyst to give 82.0% of product.

EXAMPLE 7

2 mol of ethylaminal ester (96%, remainder DMF), 3 mol of ethyl acetate and 150 ml of DMF were heated at 130° C. for 12 h in a 1.3 l V₄A autoclave. The pressure was kept at 5 bar by means of a reducing valve. After working-up by distillation, it was possible to obtain 94.8% of the theoretical yield of product.

EXAMPLE 8 (COMPARATIVE)

29.2 g of ethylaminal ester, 26.4 g of ethyl acetate and 14 g of pyrrolidine were refluxed for 6 h in 60 ml of DMF. 93.9% of the theoretical yield contained a 12:1 mixture of ethyl β-pyrrolidino- and β-dimethylaminoacrylate.

What is claimed is:

1. A process for the preparation of a β-aminoacrylic acid ester of the formula

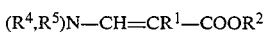

by reacting an acetic acid ester of the formula

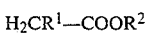

with an aminal ester of the formula

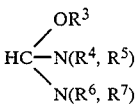

in which formulae $R^1$ is hydrogen, linear or branched $C_1$—$C_8$-alkyl, linear or branched $C_2$—$C_8$-alkenyl, $C_3$—$C_8$-cycloalkyl, $C_6$—$C_{12}$-aryl, $C_7$—$C_{10}$-aralkyl or a 5- to 8-membered aromatic or non-aromatic heterocyclic ring in which the heteroatoms are 1 or 2 from the group consisting of N, O or S, $R^2$ and $R^3$ independently of one another are linear or branched $C_1$—$C_8$-alkyl and $R^4$, $R^5$, $R^6$ and $R^7$ independently of one another are linear or branched $C_1$—$C_8$-alkyl, linear or branched $C_2$—$C_8$-alkenyl, $C_2$—$C_8$-alkoxyalkyl, $C_3$—$C_8$-alkoxyalkenyl, $C_3$—$C_8$-cycloalkyl, $C_6$—$C_{12}$-aryl, $C_7$—$C_{10}$-aralkyl or a 5- to 8-membered aromatic or non-aromatic heterocyclic ring in which the heteroatoms are 1 or 2 from the group consisting of N, O or S, it further being possible for $R^4$ and $R^5$ or $R^6$ and $R^7$, together with the N atom which they substitute, to form a 5- to 8-membered aromatic or non-aromatic N-heterocyclic ring which can contain another heteroatom from the group consisting of N, O and S, wherein the reaction is carried out in the presence of one or more catalysts from the group consisting of aromatic tertiary amines and aromatic carbinols of the formula

 (IV)

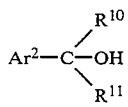

are used, in which formulae

R$^8$ and R$^9$ independently of one another have the range of meanings of R$^4$ and R$^5$ mentioned above, Ar$^1$ and Ar$^2$ independently of one another are 5- to 7-membered carbocyclic or heterocyclic aromatic radicals which can also be substituted, R$^{10}$ has the range of meanings of R$^4$ and R$^{11}$ has the range of meanings of R$^4$ or Ar$^2$, but is independent of R$^4$ and Ar$^2$, at 0.5 to 10 bar, and at 50°–170° C. in an aprotic polar solvent and the aminal ester and the acetic acid ester are used in a molar ratio of 3:1 to 1:10.

2. The process of claim 1, wherein the reaction is carried out at 1 to 5 bar.

3. The process of claim 1, wherein the reaction is carried out at 80°–150° C.

4. The process of claim 1, wherein the aprotic polar solvent is one or more from the group consisting of N-persubstituted acid amides, sulpholanes, sulphoxides and sulphones.

5. The process of claim 1, wherein R$^1$ is hydrogen or linear or branched C$_1$—C$_4$-alkyl.

6. The process of claim 5, wherein R$^1$ is hydrogen or methyl.

7. The process of claim 1, wherein R$^2$ is linear or branched C$_1$—C$_4$-alkyl.

8. The process of claim 7, wherein R$^2$ is methyl or ethyl.

9. The process of claim 1, wherein R$^3$ is linear or branched C$_1$—C$_5$-alkyl.

10. The process of claim 9, wherein R$^3$ is n- and iso-alkyl.

11. The process of claim 10, wherein R$^3$ is methyl or ethyl.

12. The process of claim 1, wherein R$^4$, R$^5$, R$^6$ and R$^7$ independently of one another are linear or branched C$_1$—C$_4$-alkyl, cyclopropyl, cyclopentyl, cyclohexyl, phenyl or benzyl, it further being possible for R$^4$ and R$^5$ or R$^6$ and R$^7$, together with the N-atom which they substitute, to form a 5- to 8-membered aromatic or non-aromatic N-heterocyclic ring which can contain another heteroatom from the group consisting of N, O and S.

13. The process of claim 12, wherein R$^4$, R$^5$, R$^6$ and R$^7$ independently of one another are linear or branched C$_1$—C$_4$-alkyl, it further being possible for R$^4$ and R$^5$ or R$^6$ and R$^7$, together with the N atom which they substitute, to be morpholino, pyrrolidino or piperidino.

14. The process of claim 1, wherein the aprotic polar solvent used is an N-persubstituted acid amide.

15. The process of claim 14, wherein the solvent is NMP, NMC, DMAC, DMF or tetramethylurea.

16. The process of claim 15, wherein the solvent is DMF.

17. The process of claim 1, wherein the aminal ester and the acetic acid ester are used in a molar ratio of 2:1 to 1:5.

18. The process of claim 17, wherein the molar ratio is 1:1 to 1:4.

* * * * *